United States Patent [19]

Reed

[11] Patent Number: 4,493,692
[45] Date of Patent: Jan. 15, 1985

[54] BLOOD GAS CONCENTRATION CONTROL APPARATUS AND METHOD

[76] Inventor: Charles C. Reed, 5934 Hornwood, Houston, Tex. 77081

[21] Appl. No.: 426,777

[22] Filed: Sep. 29, 1982

[51] Int. Cl.³ ............................................. A61M 1/03
[52] U.S. Cl. .......................................... 604/4; 604/28; 604/50; 128/635; 128/DIG. 3; 422/44
[58] Field of Search ......................................... 604/4–6, 604/28, 31, 50; 128/635, DIG. 3; 422/44, 45

[56] References Cited

U.S. PATENT DOCUMENTS

| | | | |
|---|---|---|---|
| 3,482,575 | 12/1969 | Claff et al. | 604/4 |
| 3,910,256 | 10/1975 | Clark et al. | 604/4 |
| 4,108,607 | 8/1978 | Pearson et al. | 128/DIG. 3 |
| 4,401,431 | 8/1983 | Arp | 604/4 |

*Primary Examiner*—Kyle L. Howell
*Assistant Examiner*—John C. Hanley
*Attorney, Agent, or Firm*—Workman, Nydegger & Jensen

[57] ABSTRACT

Novel methods and apparatus are provided for regulating the concentrations of oxygen and carbon dioxide in blood during extracorporeal cardiopulmonary bypass. According to the invention, probes capable of measuring the partial pressures of oxygen and carbon dioxide in blood are provided in the venous and arterial lines, both probes measuring the blood gas levels at the ambient temperature of the blood in the extracorporeal blood circuit. These concentrations are monitored on a real-time basis by a processor unit which compares the values reported by the arterial probe with selected values chosen by the perfusionist. The processor unit then preferably controls the gas flow to the oxygenator portion of the perfusion system so that the treated blood maintains the chosen concentrations of oxygen and carbon dioxide. In other embodiments, the probes are adapted to measure other perfusion variables, including temperature, hematocrit, blood flow rate, and pH, thus allowing further automation by the processor unit.

20 Claims, 4 Drawing Figures

BLOOD GAS CONCENTRATION CONTROL APPARATUS AND METHOD

BACKGROUND

1. The Field of the Invention

The present invention relates to methods and apparatus for controlling blood gas levels. More particularly, the present invention is directed to methods and apparatus for monitoring and adjusting the concentration of oxygen and carbon dioxide dissolved in blood, particularly during surgery and other medical procedures.

2. The Prior Art

In order to maintain biological activity the tissues of the body require various nutrients, and particularly oxygen. As a byproduct of this biological activity, various waste products, including carbon dioxide, are formed and must be removed from the body. The blood serves as a carrier of these nutrients to and waste products from the body tissues.

Under normal circumstances, the lungs serve to replenish oxygen to the blood and to remove excess carbon dioxide therefrom. This is accomplished because of the difference between the partial pressure of oxygen (hereinafter sometimes referred to as "$pO_2$") and the partial pressure of carbon dioxide (hereinafter sometimes referred to as "$pCO_2$") in the lungs and in the blood passing therethrough.

Typically, pulmonary arterial blood (the blood being pumped to the lungs for gas exchange) has a $pO_2$ of about 40 millimeters of mercury ("mmHg") and a $pCO_2$ of about 45 mmHg. However, the typical partial pressures of oxygen and carbon dioxide in a person's lungs are about 104 mmHg and 40 mmHg, respectively. As a result of this large difference in the partial pressure of oxygen in the lungs in comparison to that in the pulmonary arterial blood, there is a great tendency for oxygen to diffuse through the respiratory membrane of the lung alveoli into the blood. Although there is a much smaller difference between the partial pressure of carbon dioxide in the lungs and in pulmonary arterial blood, carbon dioxide diffuses much more readily than does oxygen, and thus there is also a great tendency for carbon dioxide to pass through the respiratory membrane from the blood and into the alveoli, from which it is expired. The gas exchange which takes place in the lungs is very efficient, and blood passing through the lungs typically attains a $pO_2$ and $pCO_2$ equal to that of the air in the lungs, that is, a $pO_2$ of about 104 mmHg, and a $pCO_2$ of about 40 mmHg.

Once oxygen dissolves in the blood, it quickly combines with hemoglobin contained in erythrocytes (also known as "red blood cells"). As the blood is then pumped to body tissues having a low oxygen content, oxygen dissociates from the hemogloblin and diffuses into the tissues. At the same time, excess carbon dioxide diffuses from the tissues into the blood, where about one-third of the carbon dioxide combines with hemoglobin, about half is converted to bicarbonate ion, and the remaining one-sixth remains as carbon dioxide dissolved in the blood.

The bicarbonate ion is extremely beneficial when maintained in approximately the proper concentration because it serves to buffer the pH of the blood to a pH of 7.4, which is the optimum pH for biological activity of many enzymes contained in the body. Deviating from this normal pH alters the normal metabolic functioning of these enzymes and can result in trauma or even death.

Because about half of the carbon dioxide dissolved in blood is present as bicarbonate ion, the pH of the blood is directly dependent upon the $pCO_2$. Thus, an increase in $pCO_2$ leads to a lowering of the pH of the blood, a condition known as "acidosis," and a decrease in $pCO_2$ leads to a rise in blood pH, a condition known as "alkalosis." As indicated above, either condition can lead to serious consequences because of the alteration caused in normal metabolic functioning of critical enzymes. Thus, it is important that the $pCO_2$ be kept within narrow limits, preferably within the range of about 35–45 mmHg.

The $pO_2$, on the other hand, is less critical. Under normal circumstances, as stated above, the $pO_2$ fluctuates broadly between about 104 mmHg after the blood has passed through the alveoli, and about 40 mmHg after the blood has made a circuit through the body. The $pO_2$ can actually drop to about 25 mmHg before the tissues begin receiving inadequate amounts of oxygen. At the same time, it is not dangerous to increase $pO_2$ above normal levels unless those normal levels are greatly exceeded. Thus, it is believed that $PO_2$ can, under certain circumstances, be raised to as much as about 300 mmHg without significant adverse affect.

During open heart surgical procedures, it is necessary to establish cardiopulmonary bypass in order to mechanically perform the functions normally produced by the heart and lungs. The treatment of blood extracorporeally and the administration of such treated blood to a patient is known as blood perfusion. Proper blood treatment that will result in adequate perfusion to a patient undergoing cardiopulmonary bypass requires careful balancing and adjustment of the concentration of oxygen and carbon dioxide dissolved in the blood.

Several factors are important in selecting an appropriate $pO_2$ for a given patient. For instance, under normal circumstances red blood cells make up about forty to forty-five percent (40–45%) of the blood. The percentage of red blood cells is often referred to as the hematocrit, hence, forty percent (40%) red blood cells means the blood has a hematocrit of forty (40). On the other hand, for a number of reasons, the hematocrit of a patient undergoing cardiopulmonary bypass is typically only in the range of about fifteen to thirty (15–30). Thus, since the decrease in hematocrit means that there is a corresponding decrease in the amount of hemoglobin, it is necessary to increase the $pO_2$ to insure that a sufficient amount of oxygen is available to the body.

At the same time, it is quite common during cardiopulmonary bypass for the surgeon to cause the temperature of the patient to be reduced significantly from the normal body temperature of 37° C. It is known that for every 7° C. that the body temperature is reduced, the metabolism decreases by about fifty percent (50%). As the metabolism decreases, so does the need for oxygen; hence, a lower $pO_2$ than normal will be sufficient to maintain biological activity.

Yet another important factor in selecting an appropriate $pO_2$ for blood returned to a patient after extracorporeal treatment is the flow rate of the blood; a decrease in the blood flow rate will necessitate an increase in the amount of oxygen carried by a given volume of blood, and an increase in blood flow rate will permit use of a lesser amount of oxygen carried by the same volume of blood.

Accordingly, it will be appreciated that the selection of an appropriate $pO_2$ is dependent upon many factors, and more properly, it is the amount of oxygen actually utilized by the body and the efficiency of oxygen transfer during perfusion that is important. During cardiopulmonary bypass, a $pO_2$ of arterial blood (the blood being returned to the body) in the range of about 100-200 mmHg is required to insure adequate oxygen transfer and to maintain the $pO_2$ of venous blood (that leaving the body for extracorporeal treatment) in the desired range of about 25-40 mmHg.

During the course of surgery, both venous and arterial blood samples are regularly sent to the laboratory for analysis. Typically, the information obtained are values for pH, $pCO_2$, $pO_2$, and hematocrit. Based on this information, the blood perfusionist can determine the adequacy of perfusion and thus make appropriate modifications to the extracorporeal blood treatment apparatus.

Unfortunately, it is time-consuming to send blood samples to the laboratory for analysis, and it may be as long as thirty minutes before the perfusionist obtains the test results. After analyzing these results, making what is hoped to be the proper adjustments, and then allowing the patient to stabilize for a few minutes, a new blood sample must be taken and analyzed. It is common to undercorrect or overcorrect on the basis of previous test results, yet be unaware of the improper adjustment for an additional thirty minutes. This procedure can, of course, result in serious harm to a patient. This is of particular concern when it is realized that a patient undergoing cardiac surgery is already undergoing substantial trauma and the additional trauma imposed by improper perfusion may have extremely serious consequences.

From the foregoing, it will be readily apparent that it would be a significant advancement in the art of blood perfusion to provide methods and apparatus that would provide more timely and precise control over the blood gas levels during cardiopulmonary bypass despite the variation in hematocrit, body temperature, and blood flow rate through the perfusion apparatus. Such apparatus and methods are disclosed and claimed herein.

BRIEF SUMMARY AND OBJECTS OF THE INVENTION

The present invention is directed to methods and apparatus for regulating the amount of oxygen and carbon dioxide dissolved in blood being treated extracorporeally during cardiopulmonary bypass. In the past, serious problems have often occurred due to the excessive time required to determine the proper adjustments to obtain an appropriate concentration of oxygen and carbon dioxide during extracorporeal treatment of a patient's blood during cardiopulmonary bypass. These problems have been exacerbated by the fact that such an appropriate concentration is altered by changes in such factors as the ambient temperature of the blood, blood flow rate, and hematocrit.

In accordance with the present invention, this difficulty is avoided by simultaneously measuring on a real-time basis, the $pO_2$ and $pCO_2$ of venous blood which is entering the perfusion apparatus for extracorporeal treatment and the $pO_2$ and $pCO_2$ of arterial blood being returned to the patient, and continuously adjusting the rate of addition of oxygen and removal of carbon dioxide to maintain the $pO_2$ and $pCO_2$ of the arterial blood at a desired level.

It is, therefore, a general object of the present invention to provide methods and apparatus capable of real-time regulation of the levels of oxygen and carbon dioxide in the blood.

It is another object of the present invention to provide methods and apparatus capable of regulating the levels of oxygen and carbon dioxide in the blood despite variations in factors such as hematocrit, temperature, and flow rate.

These and other objects and features of the present invention will become more fully apparent from the following description and appended claims taken in conjunction with the accompanying drawings.

DETAILED DESCRIPTION OF THE INVENTION

The present invention is directed to methods and apparatus for monitoring and adjusting on a real-time basis the concentrations of oxygen and carbon dioxide dissolved in the blood of a patient undergoing cardiopulmonary bypass so as to avoid the dangers inherent in the conventional procedure of obtaining blood gas information from a laboratory.

GENERAL DISCUSSION

The amount of oxygen utilized as blood cycles through a body may be determined by measuring the amount of oxygen in the blood as it leaves the lungs (or an oxygenator in an extracorporeal blood circuit) and comparing it to the amount of oxygen in the blood after it completes its circuit and returns to the lungs (or the oxygenator). The difference in these amounts of oxygen is the amount of oxygen actually transferred and utilized.

Since about ninety-seven percent (97%) of the oxygen carried by the blood is chemically combined with hemoglobin, it is necessary to know the amount of hemoglobin present in the patient's blood before a $pO_2$ value can be related to the quantitative amount of oxygen dissolved in the blood. As discussed above, this is typically obtained by measuring the hematocrit.

It is well-known that the amount of hemoglobin is equal to about one-third the value of the hematocrit. Since the normal hematocrit is about 45, it can thus be determined that there is typically about 15 grams of hemoglobin per 100 milliliters of blood. It has been determined experimentally that one gram of hemoglobin can bind 1.34 milliliters of oxygen (at one atmosphere pressure and at the normal body temperature of 37° C.). Thus, if the hemoglobin is 100 percent saturated with oxygen, there will be approximately 20 milliliters of oxygen bound to hemoglobin for each 100 milliliters of blood.

Figure 2:
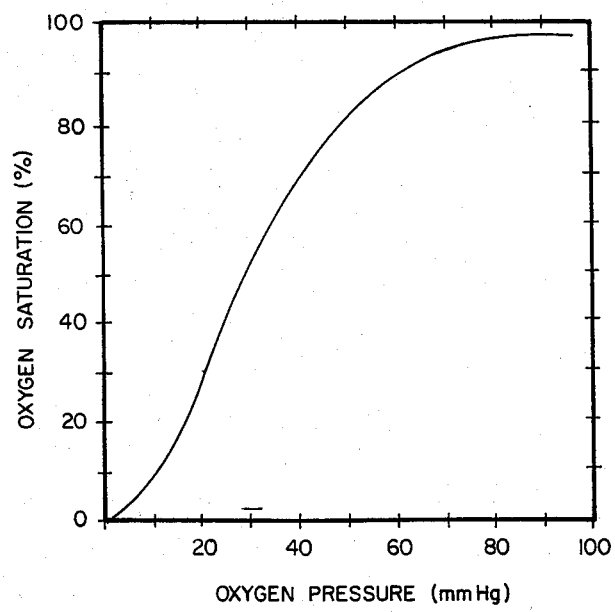
FIG. 2 is a graphical representation of the oxygen-hemoglobin dissociation curve under normal conditions and illustrates the extent of oxygen saturation of hemoglobin in the blood within a range of partial pressures of oxygen.

The saturation level of the hemoglobin is related to the partial pressure of oxygen in the blood, and an oxygen-hemoglobin dissociation curve may be drawn to illustrate this relationship. FIG. 2 shows the oxygen-hemoglobin dissociation curve which exists under normal body conditions, illustrating the effect of variations of $pO_2$ over the range of 0 to 100 mmHg on oxygen saturation of the hemoglobin in the blood.

Although not shown in FIG. 2, as the partial pressure of oxygen is increased above 100 mmHg, the oxygen saturation slowly increases until the hemoglobin actually becomes 100 percent saturated at a $pO_2$ of 760 mmHg. Thus, if one is to breathe pure oxygen it is possible to completely saturate the hemoglobin in the blood. However, at the normal arterial $pO_2$ of 104 mmHg, there is a hemoglobin saturation of only about 97.5 percent, which means that about 19.5 milliliters of oxygen are bound to hemoglobin. Similarly, the normal pulmonary arterial $pO_2$ of 40 mmHg corresponds to a saturation of about 75 percent, indicating that about 15 milliliters of oxygen is chemically bound with hemoglobin. Comparing these sets of figures, it can be seen that under normal circumstances, the body utilizes about 4.5 milliliters of oxygen from each 100 milliliters of blood.

Figure 3:
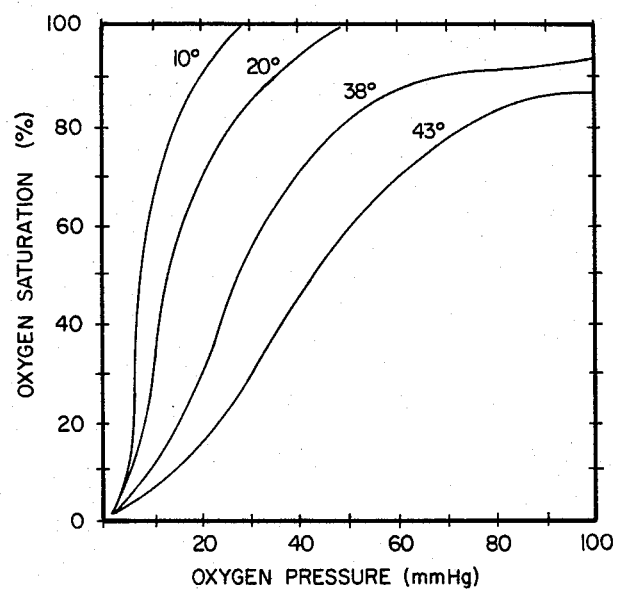
FIG. 3 is a graphical representation illustrating the effect of a change in temperature on the oxygen-hemoglobin dissociation curve of FIG. 2.
Figure 4:
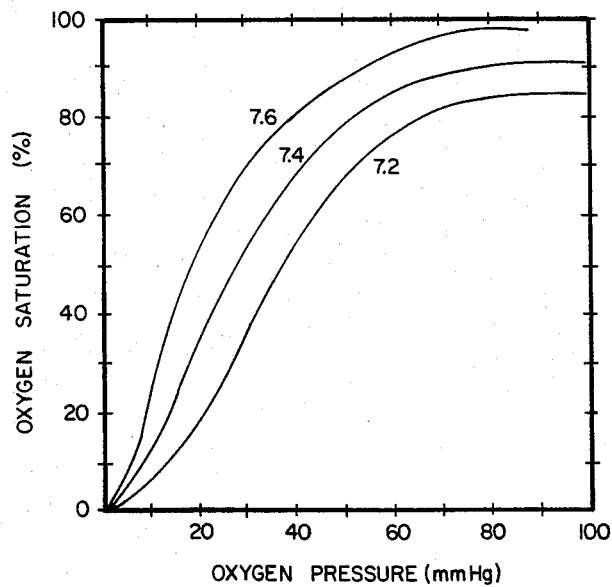
FIG. 4 is a graphical representation illustrating the effect of a change in pH on the oxygen-hemoglobin dissociation curve of FIG. 2.

It is important to look at the actual amount of oxygen utilized in a given situation rather than merely at the difference in $pO_2$, as is illustrated in FIGS. 3 and 4. This is because the oxygen-hemoglobin dissociation curve is highly sensitive to variations in temperature and pH.

Thus, FIG. 3 shows the effect of a change in temperature on the oxygen-hemoglobin dissociation curve, and FIG. 4 shows the effect of a change of pH on the normal curve.

As seen in these figures, hemoglobin has a higher than normal affinity for oxygen at lower temperatures and/or at a higher pH, so that an appropriate decrease in $pO_2$ under these conditions will not decrease the saturation level of the hemoglobin. Thus, referring to FIG. 3, if it is desired to maintain an oxygen saturation of 80%, it is necessary to maintain a $pO_2$ of about 40 mmHg when the blood temperature is 38° C., whereas the same 80% saturation may be maintained with a $pO_2$ if only about 25 mmHg when the blood temperature is reduced to 20° C. As seen from FIG. 3, this effect becomes even more pronounced at higher levels of oxygen saturation.

Conversely, at higher temperatures and/or lower pH, hemoglobin has a lower affinity for oxygen, and higher $pO_2$ levels are required to maintain a certain degree of saturation. This latter property is particularly troublesome because inadequate removal of carbon dioxide will result in a lowering of pH, which in turn reduces the level of oxygen saturation in the blood, even though the $pO_2$ appears normal.

From the foregoing, it can be seen that the partial pressure of oxygen is subject to wide variation under different conditions of temperature and pH, and it would be preferable to measure oxygen saturation directly in order to determine oxygen concentration in the blood. Unfortunately, with currently available apparatus it is impractical to measure saturation directly and that value must be determined from a correlation of the partial pressure of oxygen with the appropriate oxygen-hemoglobin dissociation curve. Nevertheless, it will be appreciated from the subsequent discussion that such apparatus may be readily incorporated into the method and apparatus of the present invention.

There have been many attempts to correlate average oxygen demand with such variables during perfusion as blood flow rate, hemoglobin concentration, and weight and size of the patient. Nevertheless, these attempts have so far proven unsatisfactory due to individual variations in blood flow distribution, the patient's response to anesthesia, and other similar considerations. Thus, it has remained necessary to monitor $pO_2$ and $pCO_2$ in order to gauge the adequacy of perfusion.

As mentioned above, the conventional method for monitoring these blood gas concentrations has been by intermittently sampling the blood flowing in the extracorporeal blood circuit and then analyzing the samples in the laboratory. Despite the universal nature of this approach, this approach is unsatisfactory because of the significant lag time between the making of an adjustment in the rate of administration of oxygen and removal of carbon dioxide until the effect of that adjustment is known. Subjecting the patient to potentially improper blood treatment during a large portion of the time that the cardiopulmonary bypass is in operation, increases the probability of injury to the patient significantly.

Further, mere handling of blood samples by a laboratory can cause changes in the $pO_2$ and $pCO_2$ of the samples, thereby reducing the accuracy of the results. Additionally, due to equipment limitations, it is standard procedure for laboratories to measure the blood gas levels at a temperature of 37° C. As mentioned heretofore, the values of $pO_2$ and $pCO_2$ decrease with an increase in temperature. Accordingly, the results of laboratory analysis can be quite misleading when the patient is maintained at a body temperature less than 37° C.

During cardiopulmonary bypass, it is typical to measure $pO_2$ and $pCO_2$ of blood in the venous return line and use those values as a basis for increasing or decreasing the amounts of oxygen and carbon dioxide supplied to the oxygenator apparatus. Yet, a large amount of blood is often collected through suction lines into a cardiotomy reservoir. Blood in the cardiotomy reservoir is likely to undergo a decrease in $pCO_2$ and an increase in $pO_2$ because the blood therein is in substantial contact with the atmosphere, which typically has a $pCO_2$ of only about 0.3 and a $pO_2$ of about 159 mmHg. As this blood from the cardiotomy reservoir mixes with the venous blood in the blood oxygenator, the $pO_2$, and the $pCO_2$ of the mix can vary over a broad range.

To create even further problems, the cardiotomy reservoir does not empty at a constant rate into the oxygenator. Rather, the cardiotomy reservoir empties into the oxygenator only as it becomes full, at which time a large volume of blood is rapidly transferred to the oxygenator. The time between each intermittent draining of the cardiotomy reservoir depends primarily on how much blood the surgeon is suctioning at any particular time. Thus, use of a cardiotomy reservoir further aggravates the problem of regulating $pO_2$ and $pCO_2$ because it is typically impossible to predict precisely what effect the addition of blood from the cardiotomy reservoir will have on the $pO_2$ and $pCO_2$ of the blood in the oxygenator.

THE PREFERRED METHODS AND APPARATUS

The present invention is designed to overcome the disadvantages inherent in the conventional perfusion equipment that result from a significant delay from the time of the taking of blood samples for analysis until the time that the results become available to the perfusionist. The present invention is also capable of monitoring $pO_2$ and $pCO_2$ at the ambient blood temperature, thus giving more accurate information than available heretofore. Further, as will be seen, the present invention allows rapid and continuous adjustment to be made to the amount of oxygen and carbon dioxide administered to the blood oxygenator, thereby preventing the large and potentially serious variations which have occurred heretofore because of the intermittent draining of a cardiotomy reservoir.

Figure 1:
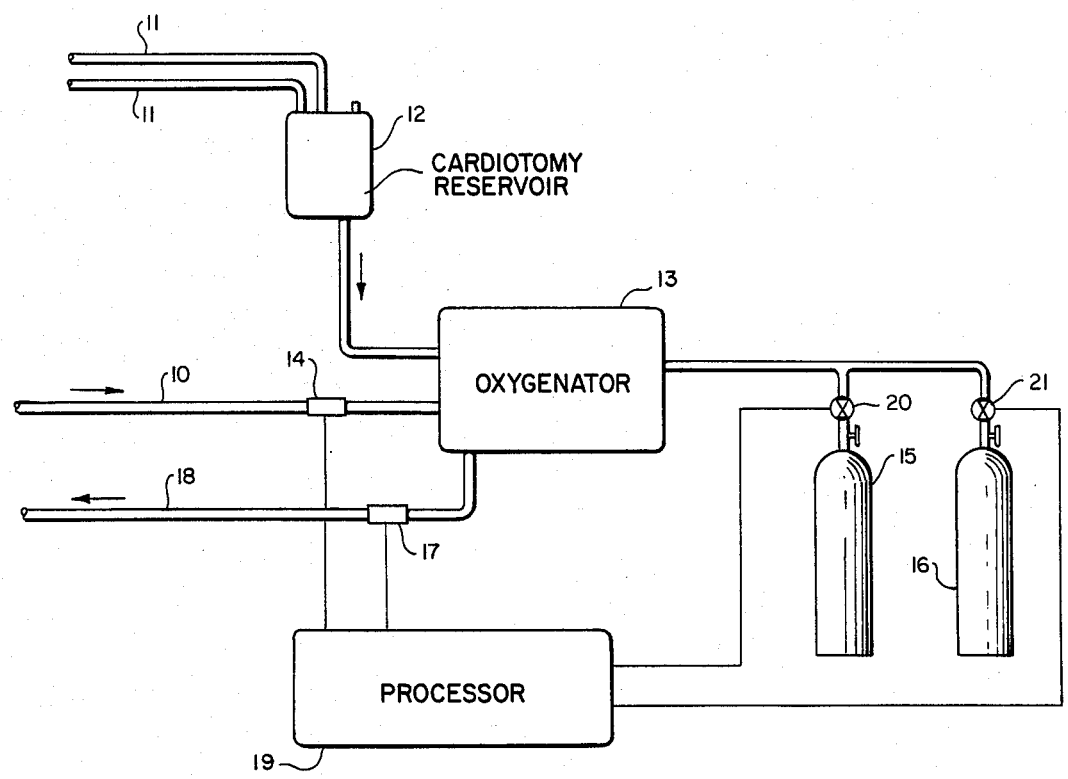
FIG. 1 is a schematic representation of a preferred embodiment of a perfusion system incorporating the present invention.

Reference is now made to the drawings wherein like parts are designated by like numerals throughout. FIG. 1 is a schematic representation showing a conventional perfusion system modified in accordance with the present invention so as to be capable of providing continuous information concerning the status of a patient's blood and of simultaneously making appropriate adjustments to the flow of oxygen and carbon dioxide administered to the blood oxygenator in order that the concentration of oxygen and carbon dioxide in the blood is maintained within the desired range.

With specific reference to FIG. 1, blood requiring treatment is carried from the patient through tubing commony referred to as venous line 10. Blood is also collected from time to time through one or more suction lines 11. Because suctioned blood generally contains a large number of air bubbles and unwanted particulate matter, the suctioned blood is generally collected in a cardiotomy reservoir 12 which aids in filtering and defoaming the blood. In order to achieve optimum defoaming, blood is generally allowed to accumulate in the cardiotomy reservoir until the reservoir reaches a predetermined level, at which time it is drained into oxygenator 13.

Although the amount of blood entering the oxygenator through venous line 10 is relatively constant, blood enters oxygenator 13 from cardiotomy reservoir 12 only intermittently; the frequency will depend upon how much blood is being collected through suction lines 11. At some stages of cardiac surgery, even more blood will be collected through suction lines 11 than through venous line 10.

In accordance with the present invention, a probe 14 is interposed in venous line 10 between the patient and oxygenator 13 such that it is possible to monitor continuously the condition of the blood leaving the patient. Such a probe is preferably constructed so as to be capable of measuring $pO_2$, $pCO_2$, pH, blood flow rate, temperature and hematocrit. Nevertheless, it is expected that a probe capable of measuring only $pO_2$ and $pCO_2$ would be sufficient to derive most of the benefit of the present invention because pH is largely dependent upon the $pCO_2$. Moreover, the blood flow rate and hematocrit are relatively constant unless there is an addition of fluid to the patient, in which case the new value may be readily determined by a one-time measurement; the ambient temperature of the blood is quite constant and is generally held at a selected temperature by a heat exchanger used in connection with the blood oxygenator device. Thus, while the present invention contemplates substantially continuous monitoring of the concentrations of oxygen and carbon dioxide in the blood both before and after extracorporeal treatment, it would be possible to measure pH, blood flow rate, hematocrit and temperature in the conventional manner.

The most common type of blood oxygenator device 13 is what is termed a "bubble oxygenator," which operates by passing a stream of gas bubbles through a column of blood. It is known that the smaller the bubbles are, the more efficient they are in transferring oxygen to the blood. Unfortunately, the converse is true with respect to the removal of carbon dioxide; it has been found that increasing the size of the gas bubbles will improve the efficiency of removal of carbon dioxide. Thus, a compromise must be struck in order to obtain reasonable efficiencies of oxygen transfer and carbon dioxide removal.

As explained above, a variety of factors can cause variations in $pO_2$ and $pCO_2$ during a surgical procedure, thus requiring adjustments to be made in the cardiopulmonary bypass system. The most common approach is to adjust the composition and flow rate of gas being fed to the oxygenator so as to regulate its ability to oxygenate and adjust the carbon dioxide concentration of the blood.

A common arrangement for supplying an adjustable composition of gas for use in the oxygenator is illustrated in FIG. 1. There, it is seen that the oxygenator is connected to parallel tanks or sources of gas, one tank 15 containing 100 percent oxygen and the other tank 16 containing a mixture of 95 percent oxygen and 5 percent carbon dioxide. Commonly, oxygen from the pure oxygen source 15 is applied at the rate of about 1-2 liters of oxygen per liter of blood flow through the oxygenator, and sufficient gas from the oxygen/carbon dioxide source 16 is administered so as to keep the blood gas concentrations in the venous blood 10 within the desired $pO_2$ and $pCO_2$ limits.

Thus, if the $pCO_2$ were to drop below the desired range, the flow of gas from tank 16 could be increased by an amount sufficient to bring the $pCOL_2$ back into limits. If the $pCO_2$ were to become too high, the flow of gas from tank 16 would be reduced. If $pO_2$ were to become too low, the flow of gas from tank 15 would be increased.

In accordance with the present invention, a probe 17 similar to probe 14 is inserted into arterial line 18 between the oxygenator and the patient. Probes 14 and 17 are connected to a processor 19 which in turn controls a pair of servo-controlled valves 20 and 21 which regulate the flow from gas sources 15 and 16, respectively, to oxygenator 13.

In one preferred embodiment, processor 19 is capable of continuously displaying the values of the properties measured by probes 14 and 17. Hence, if probes 14 and 17 are adapted to measure $pO_2$ and $pCO_2$, it is preferred that these values be continuously displayed. When using probes capable of measuring only $pO_2$ and $pCO_2$, it is also preferred that processor 19 be adapted to accept an input from the perfusionist of the desired value of $pO_2$ and $pCO_2$ of blood exiting oxygenator 13, or other values as explained below. In this manner, it is possible for processor 19 to compare the values of $pO_2$ and $pCO_2$ in the arterial blood passing through probe 17 with the desired values entered by the perfusionist, and then operate servo-valves 20 and 21 so as to bring the actual values of $pO_2$ and $pCO_2$ into conformity with the desired values thereof.

Thus, in the simple embodiment described above, the perfusionist takes into account such factors as flow rate, temperature, and hematocrit and selects what he believes to be an appropriate $pO_2$ and $pCO_2$ under the circumstances. As he obtains information from probe 14 allowing him to determine actual oxygen transfer, he can continue to evaluate the optimum setting of $pO_2$ and $pCO_2$ under the circumstances and, if needed, input new values into the processor.

This arrangement also allows adjustment to be made for the variation in $pO_2$ and $pCO_2$ caused by intermittent draining of the cardiotomy reservoir. Thus, as blood from cardiotomy reservoir 12 passes through oxygenator 13 and enters probe 17, the resultant change in $pO_2$ and $pCO_2$ will be immediately observed by processor 19, which will make appropriate adjustments to the rate of gas flow from gas sources 15 and 16. Similarly, as the flow slows and stops when the cardiotomy reservoir empties, the resulting change in $pO_2$ and $pCO_2$ will be monitored by the processor through probe 17 and again appropriate adjustments will be made to valves 20 and 21.

Accordingly, substantially immediate adjustment to the levels of $pO_2$ and $pCO_2$ in blood entering the patient through arterial line 18 will be effected as the condition of the blood gas level in blood entering oxygenator 13 changes.

Of course, it is to be appreciated that processor 19 may be adapted to also correlate information relating to temperature, pH, flow rate, and hematocrit, which information may be entered into the processor either manually by the perfusionist or automatically such as by additional components contained within probes 14 and 17. By use of microprocessor technology and appropriate hardware and/or software it is also possible to record relevant data, such as that illustrated in FIGS. 2-4, into processor 19 relating to various oxygen-hemoglobin dissociation curves which occur at different values of temperature and pH. When this is done, processor 19 may be adapted so as to calculate oxygen transfer and to select the optimum $pO_2$ and $pCO_2$ of arterial blood under the particular conditions, thus completely freeing the perfusionist from the need to calculate desired values of $pO_2$ and $pCO_2$.

Alternatively, a simpler version of processor 19 may be used in which nothing more than a display of the $pO_2$ and $pCO_2$ values of the blood in the venous and arterial lines, thereby providing the perfusionist with continuous information from which appropriate manual adjustments to the rate of flow from oxygen source 15 and oxygen/carbon dioxide source 16 can be made.

In addition to the significant improvement in the control of the $pO_2$ and $pCO_2$ values and the safety to the patient provided by the present invention, an extremely important aspect of the invention is that all measurements taken by the probes are made without additional handling of the blood and are made at the ambient temperature of the blood passing through the extracorporeal blood circuit.

As stated above, the solubility of oxygen and carbon dioxide in the blood increase with a decrease in temperature. Thus, as a patient is cooled during surgery, typically by use of a heat exchanger associated with the blood oxygentor, it is necessary to adjust the flow of gas from tanks 15 and 16 to keep the concentration of oxygen and carbon dioxide within limits. It is particularly critical to closely observe the actual $pCO_2$ during cooling because the increase in solubility of carbon dioxide can result in acidosis, even though the $pCO_2$ may look favorable when measured in a laboratory at 37° C., because excess carbon dioxide will be driven off on reheating the blood to 37° C.

Similarly, as the patient is rewarmed following surgery, the flow of gases from tanks 15 and 16 must be adjusted. Since the solubility of oxygen and carbon dioxide decreases as the temperature of the blood is raised, there is a significant danger that excessive concentrations of oxygen and carbon dioxide dissolved in the blood while at low temperaures will be released from the blood as bubbles when the temperature is raised. If these bubbles get into the body of the patient they can cause serious harm. Accordingly, it is critical that the amounts of oxygen and carbon dioxide dissolved in the blood be decreased slowly as the temperature is raised following surgery in order to prevent the formation of gas bubbles.

From the foregoing it can be seen that the present invention is a significant advancement in the art of blood perfusion by providing important improvements in the safety, effectiveness, and efficiency of blood perfusion. Not only is information obtained on a real-time basis, thereby permitting immediate and accurate adjustment to the administration of oxygen and carbon dioxide to the blood oxygenator, but this information is obtained under conditions identical to those in the perfusion system rather than under artificial laboratory conditions.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for regulating the concentrations of oxygen and carbon dioxide dissolved in blood in an extracorporeal blood circuit, said apparatus comprising:
   means for collecting blood from a patient for extracorporeal treatment;
   means for monitoring in the extracorporeal blood circuit the concentrations of oxygen and carbon dioxide in the blood prior to extracorporeal treatment;
   means for oxygenating the blood;
   means for adjusting the concentration of carbon dioxide in the blood;
   means for monitoring in the extracorporeal blood circuit the concentrations of oxygen and carbon dioxide in the blood after extracorporeal treatment; and
   means for returning the blood to the patient after extracorporeal treatment.

2. An apparatus for regluting the concentrations of oxygen and carbon dioxide dissolved in blood as defined in claim 1 further comprising means for controlling the oxygenation means and means for controlling the adjusting means so that the concentrations of oxygen and carbon dioxide in the blood, as measured by the post-treatment monitoring means, are brought into substantial conformity with optimum concentrations of oxygen and carbon dioxide in the blood being returned to the patient.

3. An apparatus for regulating the concentrations of oxygen and carbon dioxide dissolved in blood as defined in claim 1 wherein the respective monitoring means monitor the concentrations of oxygen and carbon dioxide in the patient's blood at the temperature of the blood in the extracorporeal blood circuit.

4. An apparatus for regulating the concentrations of oxygen and carbon dioxide dissolved in blood as defined in claim 2 further comprising means for determining the optimum concentrations of oxygen and carbon dioxide in blood being returned to the patient, said determining means including means for correlating the concentrations of oxygen and carbon dioxide in the blood measured by the respective monitoring means with the concentration of hemoglobin in the blood, the blood flow rate, and the temperature of the blood in the extracorporeal blood circuit.

5. An apparatus for regulating the concentrations of oxygen and carbon dioxide dissolved in blood as defined in claim 4, further comprising means for monitoring the blood temperature and means for communicating said blood temperature to the correlating means.

6. An apparatus for regulating the concentrations of oxygen and carbon dioxide dissolved in blood as defined in claim 4, further comprising means for monitoring blood flow rate and means for communicating said flow rate to the correlating means.

7. An apparatus for regulating the concentrations of oxygen and carbon dioxide dissolved in blood as defined in claim 4, further comprising means for monitoring hemoglobin concentration in the blood and means for communicating said hemoglobin concentration to the correlating means.

8. An apparatus for regulating the concentrations of oxygen and carbon dioxide in blood in an extracorporeal blood circuit, said apparatus comprising:
  means for monitoring the concentrations of oxygen and carbon dioxide in blood collected for extracorporeal treatment, said monitoring being accomplished at the temperature of the blood in the extracorporeal blood circuit;
  means for extracorporeally treating the blood collected from the patient, said treatment means including means for adjusting the concentrations of oxygen and carbon dioxide in the blood;
  means for monitoring the concentrations of oxygen and carbon dioxide in the blood after treatment said monitoring being accomplished at the temperature of the blood in the extracorporeal blood circuit; and
  means for controlling the treatment means, said control means including means for comparing the concentrations of oxygen and carbon dioxide in the treated blood as measured by the post-treatment monitor means with optimum concentrations therefor, and means for bringing the measured values into conformity with the optimum concentrations.

9. An apparatus for regulating the concentrations of oxygen and carbon dioxide in blood as defined in claim 8, wherein the control means determines the optimum concentrations of oxygen and carbon dioxide by correlating the temperature of the blood in the extracorporeal blood circuit, the hemoglobin concentration, the blood flow rate, and the concentrations of oxygen and carbon dioxide in the blood collected from the patient as measured by the pre-treatment monitor means.

10. An apparatus for regulating the concentrations of oxygen and carbon dioxide in blood as defined in claim 9, further comprising means for monitoring the temperature of the blood and means for communicating such temperature to the control means.

11. An apparatus for regulating the concentrations of oxygen and carbon dioxide in blood as defined in claim 9, further comprising means for monitoring the blood flow rate and means for communicating such flow rate to the control means.

12. An apparatus for regulating the concentrations of oxygen and carbon dioxide in blood as defined in claim 9 further comprising means for monitoring the concentration of hemoglobin in the blood and means for communicating such information to the control means.

13. A method for regulating the concentrations of oxygen and carbon dioxide dissolved in blood in an extracorporeal blood circuit, the method comprising the steps of:
  collecting blood from a patient for extracorporeal treatment;
  monitoring in the extracorporeal blood circuit the concentrations of oxygen and carbon dioxide in the blood prior to extracorporeal treatment;
  oxygenating the blood;
  adjusting the concentration of carbon dioxide in the blood;
  monitoring in the extracorporeal blood circuit the concentrations of oxygen and carbon dioxide in the blood after extracorporeal treatment; and
  returning the blood to the patient after extracorporeal treatment.

14. A method for regulating the concentrations of oxygen and carbon dioxide dissolved in blood as defined in claim 13 further comprising the steps of controlling the extent of oxygenation and controlling the adjustment of carbon dioxide concentration so that the concentrations of oxygen and carbon dioxide in the blood after extracorporeal treatment are brought into substantial conformity with optimum concentrations of oxygen and carbon dioxide in the blood being returned to the patient.

15. A method for regulating the concentrations of oxygen and carbon dioxide dissolved in blood as defined in claim 13 further comprising the steps of:
  selecting optimum concentrations of oxygen and carbon dioxide for blood being returned to the patient;
  comparing said optimum concentrations with the concentrations measured in the post-treatment blood; and
  controlling the extent of oxygenation and the adjustment of carbon dioxide concentration so as to bring the post-treatment concentrations into substantial conformity with said optimum concentrations.

16. A method for regulating the concentrations of oxygen and carbon dioxide dissolved in blood as defined in claim 13 wherein the monitoring steps monitor the concentrations of oxygen and carbon dioxide in the patient's blood at the temperature of the blood in the extracorporeal circuit.

17. A method for regulating the concentrations of oxygen and carbon dioxide dissolved in blood as defined in claim 15 wherein the optimum concentrations of oxygen and carbon dioxide in the blood being returned to the patient are selected by correlating the concentration of hemoglobin in the blood, the blood flow rate, the temperature of the blood in the extracorporeal blood circuit, and the concentrations of oxygen and carbon dioxide in the blood prior to treatment.

18. A method for regulating the concentration of oxygen and carbon dioxide in blood in an extracorporeal blood circuit, the method comprising the steps of:

monitoring in the extracorporeal blood circuit the concentrations of oxygen and carbon dioxide in blood collected from a patient for extracorporeal treatment;

monitoring in the extracorporeal blood circuit the concentrations of oxygen and carbon dioxide in the blood after extracorporeal treatment;

determining optimum concentrations for oxygen and carbon dioxide in treated blood based upon the concentrations thereof in the pre-treated and post-treated blood;

comparing the concentrations of oxygen and carbon dioxide in the post-treated blood with the optimum concentrations; and adjusting the amount of oxygen added to and the amount of carbon dioxide removed from the blood during treatment so as to maintain the optimum concentrations of oxygen and carbon dioxide in the blood being returned to the patient.

19. A method for regulating the concentrations of oxygen and carbon dioxide in blood as defined in claim 18 wherein the monitoring steps are performed at the temperature of the blood in the extracorporeal blood circuit.

20. A method for regulating the concentrations of oxygen and carbon dioxide in blood as defined in claim 19 further comprising the steps of:

monitoring the temperature of the blood in the extracorporeal blood circuit;

monitirong the blood flow rate through the extracorporeal blood circuit;

monitoring the hemoglobin concentration in the blood; and correlating the blood temperature, flow rate, and hemoglobin concentration with the pre-treatment and post-treatment concentrations of oxygen and carbon dioxide when determining the optimum concentrations for oxygen an carbon dioxide in treated blood.

* * * * *

UNITED STATES PATENT AND TRADEMARK OFFICE
CERTIFICATE OF CORRECTION

PATENT NO. : 4,493,692
DATED : January 15, 1985
INVENTOR(S) : Charles C. Reed

It is certified that error appears in the above-identified patent and that said Letters Patent is hereby corrected as shown below:

Column 5, line 44, "if only" should be --of only--

Column 7, line 26, "commony" should be --commonly--

Column 9, line 20, "effected" should be --affected--

Column 10, line 55, "regulting" should be --regulating--

Column 11, line 43, "treatment said" should be --treatment, said--

Column 14, line 19, "an" should be --and--

Signed and Sealed this

Ninth Day of July 1985

[SEAL]

Attest:

DONALD J. QUIGG

Attesting Officer     Acting Commissioner of Patents and Trademarks